US008660859B1

(12) United States Patent
Ansari et al.

(10) Patent No.: US 8,660,859 B1
(45) Date of Patent: *Feb. 25, 2014

(54) SYSTEMS AND METHODS FOR EXECUTING AN ELECTRONIC PHARMACY PROGRAM THAT REQUIRES ACCESS TO AN ELECTRONIC MEDICAL RECORD

(75) Inventors: Mohsin Ovais Ansari, Highland Park, IL (US); John W. Rickord, Wheaton, IL (US)

(73) Assignee: Walgreen Co., Deerfield, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/354,701

(22) Filed: Jan. 20, 2012

(51) Int. Cl.
G06Q 10/00 (2012.01)
G06Q 50/00 (2012.01)

(52) U.S. Cl.
USPC .................................. 705/2; 705/3

(58) Field of Classification Search
USPC ........................................ 705/2, 3
See application file for complete search history.

(56) References Cited

U.S. PATENT DOCUMENTS

2002/0035618 A1* 3/2002 Mendez et al. ............... 709/219
2003/0128822 A1* 7/2003 Leivo et al. ................ 379/93.02
2004/0102931 A1* 5/2004 Ellis et al. .................... 702/188
2004/0249677 A1 12/2004 Datta et al.
2006/0277076 A1* 12/2006 Hasan et al. .................... 705/3
2008/0183495 A1* 7/2008 Butterfield et al. .............. 705/2
2009/0037224 A1* 2/2009 Raduchel ........................ 705/3
2009/0150292 A1* 6/2009 Trinh et al. .................... 705/55

* cited by examiner

Primary Examiner — Neha Patel
(74) Attorney, Agent, or Firm — Francis C. Kowalik; Marshall, Gerstein & Borun LLP; Randall G. Rueth

(57) ABSTRACT

In a pharmacy computing network, executing an electronic pharmacy program that requires access to an electronic medical record (EMR) may include determining that the execution of the pharmacy program requires data that is accessible via an EMR of a patient. The EMR may be stored in a different computing network that supports a protocol different than a protocol supported by the pharmacy network. A request for the EMR data may be generated by pharmacy network using a first protocol. A response to the request that includes the EMR data may be received by the pharmacy network using the first protocol, where the EMR data was accessed by the different network using a second protocol. The electronic pharmacy program may be executed using the EMR data included in the response. The first protocol may be based on an NCPDP standard, and the second protocol may be based on an HL7 protocol.

15 Claims, 7 Drawing Sheets

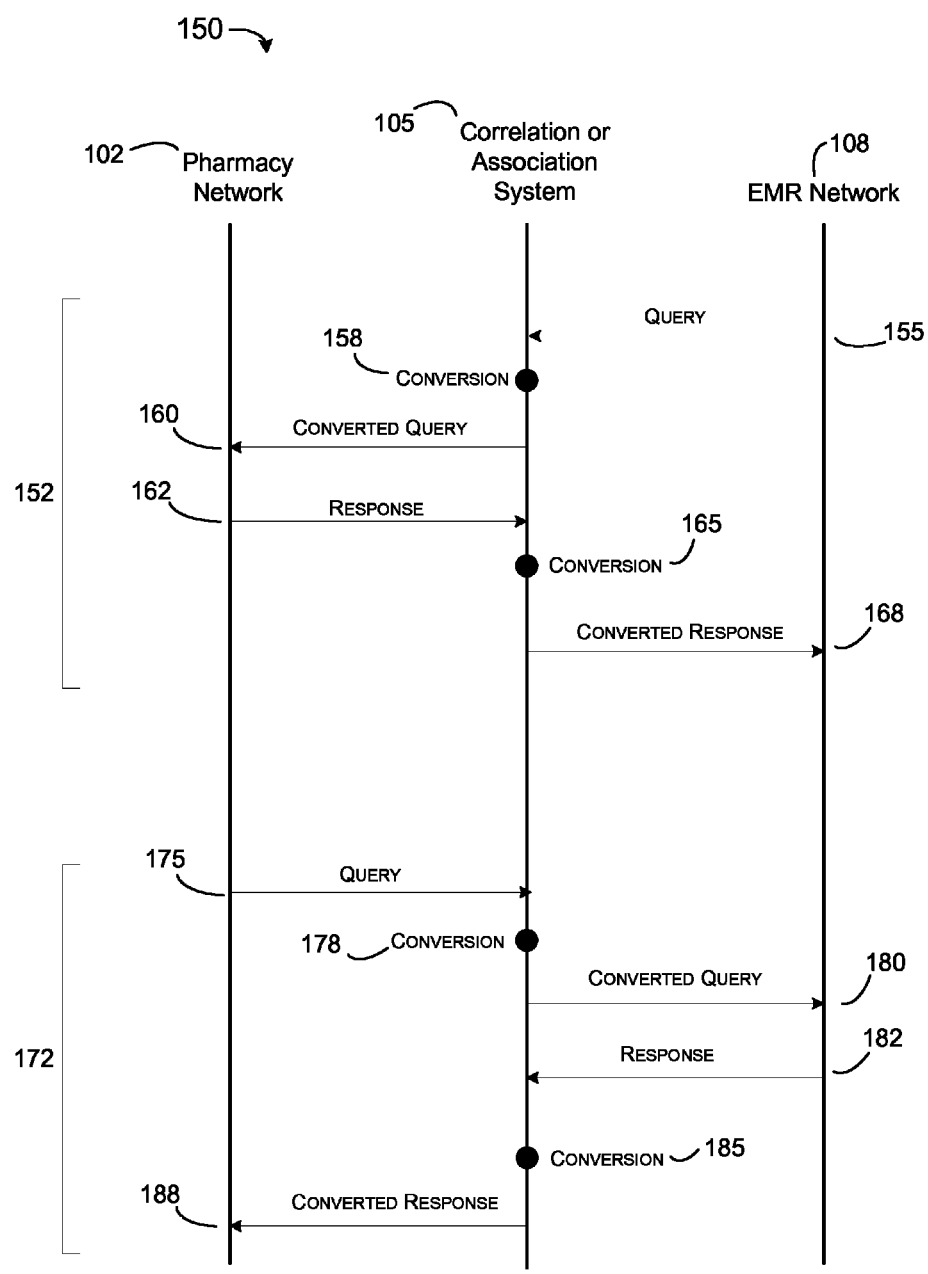

SYSTEMS AND METHODS FOR EXECUTING AN ELECTRONIC PHARMACY PROGRAM THAT REQUIRES ACCESS TO AN ELECTRONIC MEDICAL RECORD

FIELD AND BACKGROUND OF THE DISCLOSURE

1. Technical Field

The instant disclosure generally relates to electronic pharmacy programs that require access to electronic medical records of patients.

2. Background

Health care costs have been increasing at a fast rate. In an attempt to reform health care, legislation in the United States that includes incentivizing payors and providers to cooperate has been passed. As such, healthcare providers are changing their approaches to providing health care to patients. Coordination of health care across multiple health care providers or health care organizations may not only decrease the cost of health care to payors, but may also improve the quality of health care to patients. Health care organizations may include pharmacy entities or enterprises that fill or provide prescription products and services, hospitals, health care data repositories, managed care organizations, physicians and/or physician groups, therapists, and other medical professionals.

BRIEF SUMMARY OF THE DISCLOSURE

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

An embodiment of a method of executing electronic pharmacy programs that require access to electronic medical records may include determining, in a pharmacy network, that an execution of at least a part of an electronic pharmacy program requires data that is stored in or accessible via an electronic medical record (EMR) corresponding to a patient. Contents of the electronic medical record may be accessed using a first protocol which is not supported by the pharmacy network. The method may further include initiating a transmission of a request for the data included in the EMR. The request may be compatible with a second protocol that is supported by the pharmacy network and that is different from the first protocol. Additionally, the method may include receiving, at the pharmacy network, a response to the request, the response being compatible with the second protocol supported by the pharmacy network and including the requested data, where the requested data was accessed from the EMR using the first protocol. The method may include executing, by the pharmacy network, the at least the part of the electronic pharmacy program using the requested data included in the response.

Embodiments of a system for executing electronic pharmacy programs requiring access to electronic medical records may include a pharmacy computing network. The pharmacy computing network may include one or more computing devices that are communicatively coupled and a network connection to a second network different from the pharmacy computing network. Each of the one or more computing devices may transmit communications to the second network using the network connection. Each of the one or more computing devices may include one or more processors and one or more memories including one or more tangible, non-transitory computer-readable storage media. Computer-executable instructions may be stored on the one or more memories and may be executable by the one or more processors to determine that an execution of at least a part of an electronic pharmacy program requires data from an electronic medical record (EMR) corresponding to a patient, initiate a transmission of a query for the data from the EMR, receive a response that includes the requested data from the EMR, and execute the at least the part of the electronic pharmacy program using the received data. The electronic medical record may stored in a storage device included in the second network, and the pharmacy network and the second network may be conversant in different protocols and may access data stored respectively therein using different access formats, protocols and/or standards. As such, the communications transmitted from and received by the pharmacy network may be based on a first protocol, while the data from the EMR that is requested by the pharmacy network may be accessed in the second network based on a second protocol different from the first protocol.

Embodiments of a system for executing electronic pharmacy programs that require access to electronic medical records may include a data storage device storing a pharmaceutical or pharmacy record corresponding to a patient, and one or more computing devices coupled to the data storage device. The one or more computing devices may be configured to initiate an execution of an electronic pharmacy program, where the execution of at least a part of the electronic pharmacy program utilizes or is based on data included in the pharmaceutical or pharmacy record corresponding to the patient. The one or more computing devices may be further configured to determine that an execution of at least the same part or a different part of the electronic pharmacy program requires data that is included in an electronic medical record (EMR) corresponding to the patient, and to initiate, using a first protocol, a transmission of a request for the data included in the EMR. The one or more computing devices may be further configured to receive the requested data using the first protocol, where the requested data was accessed from the EMR using a second protocol. The one or more computing devices may be still further configured to execute the at least the part of the electronic pharmacy program based on the received data.

BRIEF DESCRIPTION OF SEVERAL VIEWS OF THE DRAWINGS

FIGS. 3A-3D illustrate example process flows that may be used in conjunction with executing electronic pharmacy programs that require access to electronic medical records.

DETAILED DESCRIPTION OF THE PREFERRED EMBODIMENTS

Figure 1:
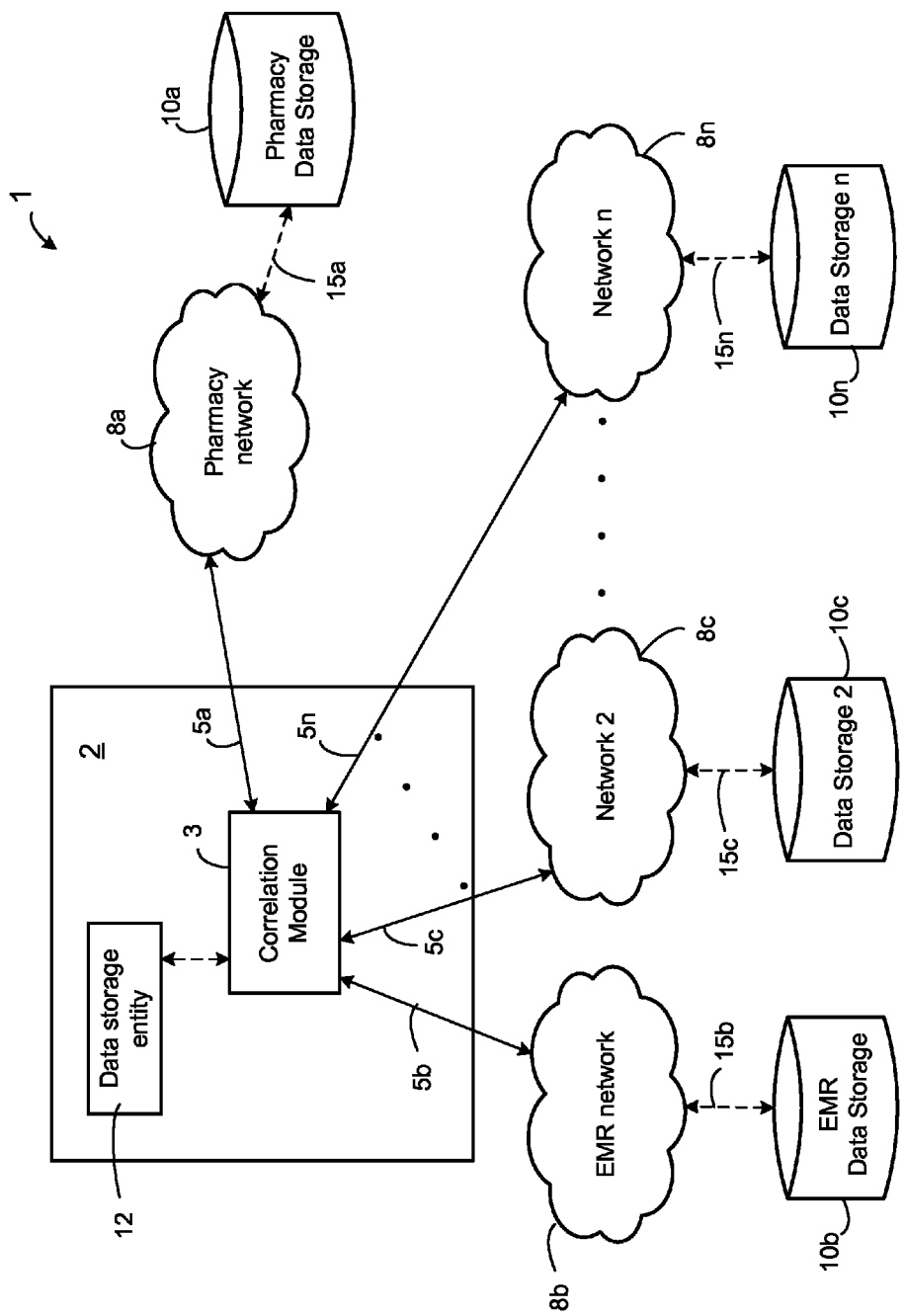
FIG. 1 is a block diagram of an example system for accessing electronic medical records, in which a system for executing pharmacy programs that require access to electronic medical records may operate.

Although the following text sets forth a detailed description of numerous different embodiments, it should be understood that the legal scope of the description is defined by the words of the claims set forth at the end of this patent and equivalents. The detailed description is to be construed as exemplary only and does not describe every possible embodiment since describing every possible embodiment would be impractical. Numerous alternative embodiments could be implemented, using either current technology or technology developed after the filing date of this patent, which would still fall within the scope of the claims.

It should also be understood that, unless a term is expressly or explicitly indicated as being defined in this patent, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. §112, sixth paragraph.

Any or all of the contents of the present disclosure may operate in conjunction with any or all of the contents of the disclosure of co-pending U.S. patent application Ser. No. 13/354,581 entitled "SYSTEMS AND METHODS OF CORRELATING ELECTRONIC PHARMACY DATA AND ELECTRONIC MEDICAL RECORDS" and filed concurrently herewith, the contents of which are hereby incorporated by reference in their entirety.

As used herein, the term "pharmacy enterprise" and "pharmacy company" are used interchangeable to refer to a company, enterprise or organization that is licensed to fill prescriptions and/or dispense prescribed pharmaceutical products such as drugs, medicaments, durable medical equipment, and the like. A pharmacy enterprise or company may provide pharmaceutical or pharmacy services such as taking prescription orders, providing oversight over prescription dispensing activities, monitoring drug therapies, counseling patients on the proper use and potential adverse events of dispensed medication, and/or other services. A pharmacy enterprise or company may be commercial or not-for-profit, and may provide or vend other products and services in addition to prescribed pharmaceutical or pharmacy products and associated pharmaceutical or pharmacy services. A pharmacy enterprise or company may have one or more physical locations or facilities, including a local store front, a space within another commercial or not-for-profit enterprise (e.g., within a store, hospital, school, nursing home, etc.), a mail-order center, a call-in center, a warehouse, a distribution center, a mobile location, or an Internet or computer-order center. Generally, a pharmacy enterprise or company may employ or contract pharmacists that are licensed to practice pharmacy, pharmacy technicians, and other personnel.

Further, as used herein, the term "pharmacy enterprise computing system," "pharmacy company computing system," "pharmacy enterprise computer system," "pharmacy company computer system," "pharmacy computer system," or "pharmacy computing system" generally refers to a computing system that is owned and/or operated by a pharmacy enterprise or company to aid pharmacy enterprise personnel to fill and dispense prescribed pharmaceutical products and other products. A pharmacy enterprise computing system may include at least one computing device, and may further include at least one database, display device, and/or user interface device. The terms "pharmacy network," "pharmaceutical network," "pharmacy computer network," "pharmacy computing network," "pharmaceutical computing network," "pharmacy company network," and "pharmacy enterprise network" are interchangeably used herein to refer to a pharmacy enterprise or company computing system that includes more than one networked computing device. Typically, but not necessarily, different physical locations of a pharmacy enterprise or company may include respective computing devices, each of which is communicatively coupled to a pharmacy computing network.

A "health care organization," as used herein, refers to a health care related enterprise or health care provider. The health care organization may be for profit or not-for-profit. The health care organization may provide health care diagnostic, therapeutic, rehabilitation, and/or other services to patients. For example, the health care organization may provide physician care, therapy, imaging, counseling, or the like. The health care organization may provide inpatient and/or outpatient services, may include one or more physical locations or facilities. Additionally or alternatively, the health care organization may provide other health-care related services, such as providing billing management, providing health care insurance, maintaining electronic medical records, etc. Examples of health care organizations may include a hospital group, a medical practice group, an insurance group, a stand-alone imaging facility, a home-health service provider, and others. In some embodiments, a health care organization may include a pharmacy enterprise.

Further, as used herein, the term "health care organization computing system" or "health care computing system" generally refers to a computing system that is owned and/or operated by a health care organization to aid the health care organization in performing tasks required by the nature of the health care organization. For example, a health care computing system may enable a representative of the health care computing system to enter and maintain electronic medical records for a patient base. A health care computing system may include at least one computing device and may further include at least one database, display device, and/or user interface device. The terms "health care computing network," "health care organization computing network," and "health care computing system network" are interchangeably used herein to refer to a health care computing system that includes more than one networked computing device. Typically, but not necessarily, different physical locations of a health care computing system may include respective computing devices, each of which is communicatively coupled to a health care computing system network.

FIG. 1 is a block diagram of an example system 1 for accessing electronic medical records, in which embodiments of a system or pharmacy network for executing pharmacy programs that require access to electronic medical records may operate. The system 1 may aid in improving the coordination of patient health care between a pharmacy enterprise and another health care organization or provider, so that the quality of health care increases while the costs of the health care decrease. Currently, a patient, health care organization representative or other human being(s) must be relied upon to determine the need to initiate an information exchange between a pharmacy enterprise and another health care organization or provider. Information flow between health care organizations may be stifled and significant amounts of time and money may be required to back-track and review actions across various health care organizations. For example, when a pharmacy enterprise generates a bill corresponding to a patient's filled prescription, to properly assess charges, a representative of the pharmacy enterprise is forced to initiate an electronic or manual communication with a prescribing physician's office and the prescribing physician's office must check the patient's EMR to determine the patient's current eligibility for various government assistance programs, Finally, the representative of the prescribing physician's office must report the information back to the pharmacy enterprise. This and other similar cumbersome processes may be fraught with time delays and human error, and thus may increase costs and expenses of health care, not to mention increase the chance of potentially harmful effects on patient treatment, such as when a patient declines a prescription based on an erroneous potential cost of the prescription.

On the other hand, the system 1 for accessing EMRs may automatically coordinate information flow between a pharmaceutical provider and a health care organization to better manage a patient's health care. In particular, the system 1 may correlate electronic pharmacy data and electronic medical record data of a patient, and in particular, between a pharmacy network storing the electronic pharmacy data and a second network (e.g., a health care organization's network) storing the patient's electronic medical records. Using the system 1, pertinent and potentially time critical health care information corresponding to a patient and stored in electronic medical records may be easily, efficiently, accurately and more timely obtained. As such, information flow between health care providers and other organizations is much faster and much less prone to costly errors.

Turning to FIG. 1, the system 1 for accessing electronic medical records may include a correlation system 2 having a correlation module 3 that is communicatively coupled by a first link 5a to a pharmacy network 8a. The pharmacy network 8a may be or may include a system for executing pharmacy programs that require access to electronic medical records, in an embodiment. The pharmacy network 8a may include a computing network such as a private network, a public computing network, or some combination of the two. At least a portion of the pharmacy network 8a may be privately administered, managed, and/or secured by a pharmacy enterprise and may be firewalled or otherwise protected from public networks and unauthorized access. The pharmacy network 8a may be a client-server network, a peer-to-peer network, an Ethernet network, a cloud computing network, or any other known type of network in which computing devices are enabled to communicate. In some embodiments, the network 8a may utilize more than one different type of networking technology. The pharmacy network 8a may be included in at least a portion of a pharmacy enterprise computing system.

The pharmacy network 8a may, in turn, be communicatively coupled to a pharmacy data storage entity or device 10a that may store pharmaceutical or pharmacy records corresponding to patients. The pharmacy data storage entity or device 10a, in an embodiment, may be communicatively coupled to more than one computing device of the pharmacy network 8a.

A pharmaceutical or pharmacy record of a patient may include information corresponding to interactions of the patient with the pharmacy enterprise, including information corresponding to prescriptions, fill dates, fill locations, refills, costs, Drug Utilization Review (DUR) results, records of pharmacist consultations, out of pocket payments, insurance or third party payments, etc. Privacy of patients' pharmaceutical or pharmacy records may be privacy protected according to local and/or federal government laws and regulations. Data other than pharmaceutical or pharmacy records may also be stored in the pharmacy storage entity 10a, in some embodiments.

Although the embodiment shown in FIG. 1 illustrates the pharmacy data storage entity 10a as external to and communicatively connected to the pharmacy network 8a, in some embodiments, the pharmacy data storage entity 10a may be included within the pharmacy network 8a. The pharmacy data storage entity 10a may include one or more data storage devices of any known non-transitory, tangible, computer-readable storage media technology, e.g., disks, solid state devices, data banks, servers, cloud storage, etc.

The correlation module 3 may be communicatively coupled by a second link 5b to an electronic medical record (EMR) network 8b. The electronic medical record network 8b may be a computing network such as a private network, a public network, or some combination of the two. At least a portion of the electronic medical record network 8b may be privately administered by a health care organization other than the pharmacy enterprise corresponding to the pharmacy network 8a, and the electronic medical record network 8b may be firewalled or otherwise protected from public networks and unauthorized access. The electronic medical record network 8b may be a client-server network, a peer-to-peer network, an Ethernet network, a cloud computing network, or any other known type of network in which computing devices are enabled to communicate. In some embodiments, the electronic medical record network 8b may utilize more than one different type of networking technology. The electronic medical record network 8b may be included in at least a portion of a health care computing system.

The EMR network or EMR computing network 8b may, in turn, be communicatively coupled to an EMR data storage entity or device 10b that may store electronic medical records corresponding to patients. An electronic medical record corresponding to a particular patient may be an electronic data file and may be used in lieu of or in addition to standard paper or film medical records to maintain information that pertains to health care of the particular patient. Information or data stored in an EMR may include, for example, dates of physician visits, symptoms, vital signs, consultations, diagnoses, tests and test results, courses of therapies and therapy results, etc. Privacy of patients' EMRs may be privacy protected according to local and/or federal government laws and regulations. Although the embodiment shown in FIG. 1 illustrates the EMR data storage entity 10b as being external to and communicatively connected to the EMR network 8b, in some embodiments, the EMR data storage entity 10b may be included within the EMR network 8b. The EMR data storage entity 10b may include one or more data storage devices of any known non-transitory, tangible, computer-readable storage media technology, e.g., disks, solid state devices, data banks, servers, cloud storage, etc.

Turning back to the correlation system 2, in some embodiments, the correlation module 3 may be communicatively coupled via at least one other link 5c-5n to a respective at least one other health care network 8c-8n. Each other health care network 8c-8n may include or be communicatively coupled to respective data storage entities or devices 10c-10n, in a manner similar to that discussed for the EMR network 8b, or in a different suitable manner. At least one of the other networks 8c-8n may be a pharmacy network different from the pharmacy network 8a, e.g., a pharmacy network corresponding to a pharmacy enterprise other than the pharmacy enterprise associated with the pharmacy network 8a.

As previously discussed, the pharmacy network 8a may be administered, managed, and/or secured by a pharmacy enterprise that is licensed or otherwise permitted to fill prescriptions, and the EMR network 8b may be administered, managed, and/or secured by a health care organization or health care provider other than the pharmacy enterprise, e.g., a hospital, a doctors' office, a medical records repository, a billing service enterprise, or the like. As such, each of the networks 8a and 8b may be a separate and independent network, and each of the networks 8a and 8b may be separately and independently managed by their respective managing or responsible enterprise or organization. Typically, each of the networks 8a and 8b may be separately secured for privacy and legal purposes by their respective enterprise or organization. For example, access to each of the networks 8a, 8b may require respective passwords, biometric identification or other means of security. In some embodiments, each of the networks 8a, 8b may reside within a respective firewall. In a similar fashion, each of the other health care networks 8c-8n may be managed by each of their respective health care organizations, such as other hospitals, medical groups, imaging centers, health insurance providers, or other health care organizations.

The correlation module 3 may be communicatively connected to a data storage entity or device 12. The data storage entity 12 may store, in one or more databases, data corresponding to each of the networks 8a-8n, in an embodiment. Additionally or alternatively, the data storage entity 12 may store data corresponding to one or more patients, such as in the same one or more databases that store the network data, and/or in different one or more databases. Although FIG. 1 illustrates the data storage entity 12 as being locally accessed by the correlation module 3, in some embodiments, the data storage entity 12 may be remotely accessed, e.g., via a link (not shown).

The pharmacy network 8a may be operatively connected to the pharmacy database or storage entity 10a via a link 15a. Similar to the link 5a, the link 15a may be any type of link known in the art. In some embodiments, the link 15a may be a link to another public or private network by which the pharmacy data storage 10a may be accessed, and the processor 5 may access the pharmacy data store 10a via the network. In some embodiments, the pharmacy data store 10a may be contained within the pharmacy network 8a itself as a networked data storage device, or the pharmacy data storage entity 10a may be contained within a memory of a computing device included in the pharmacy network 8a. In these embodiments, the link 15a may be as simple as a memory access function, an Ethernet connection, or the like. In some embodiments, the pharmacy data storage entity or device 10a may be a multiplicity of databases, data storage entities, or data storage devices. Typically, but not necessarily, the pharmacy data storage entity 10a is protected from public access. The pharmacy database 10a may be included in at least a portion of a pharmacy enterprise computing system.

Similarly, one or more of the EMR and other health organization networks 8b-8n may be operatively connected to a respective database or data storage entity 10b-10n via a respective link 15b-15n. Similar to the link 15a, each of the respective links 15b-15n may be any type of link known in the art. In some embodiments, the respective links 15b-15n may be links to another respective network via which the respective data storage entities 10b-10n may be accessed (e.g., the Internet, a virtual private network, or other suitable network). In these embodiments, the one or more networks 8b-8n may access its respective data store 10b-10n via the other respective network. In some embodiments, rather than being remotely accessed, at least one of the data storage entities 10b-10n may be contained within the network 8b-8n as a network data storage device or within a memory of a computing device included in the corresponding network 8b-8n for essentially local access. In some embodiments, one or more of the data storage entities 10b-10n may be a multiplicity of databases or data storage entities. Typically, but not necessarily, the data storage entities 10b-10n are protected from public access.

In some embodiments, the correlation system 2 may be disposed between the pharmacy network 8a and the EMR network 8b, such as when the system 2 is a server or is one or more computing devices that is networked to both the pharmacy network 8a and to the EMR network 8b. In some embodiments, the correlation system 2 may be included within the pharmacy network 8a. For example, the correlation system 2 may be included on a server or group of servers within the pharmacy network 8a, so that all computing devices corresponding to pharmacy locations within the pharmacy network 8a are serviced, for correlation purposes, by the server or group of servers on which the correlation system 2 is included. In another example, a separate instance of the correlation system 2 may be included in each computing device at each pharmacy location of the pharmacy computing system within the pharmacy network 8a. In some embodiments, a first instance of the correlation system 2 may be included on each computing device of a first set of computing devices that correspond to a first set of respective pharmacy locations within the pharmacy network 8a, while a second set of computing devices that correspond to other respective pharmacy locations may be serviced, for correlation purposes, by a single server or group of servers that is included in the pharmacy network 8a and on which an instance of the correlation system 2 is stored.

Generally, the communication format used between the correlation system 2 and the EMR network 8b and the communication format used between the correlation system 2 and the pharmacy network 8a may utilize electronic communications such as messages, file transfers, or any suitable protocol. Typically, however, the protocol used between the correlation system 2 and the EMR network 8b and the protocol used between correlation system 2 and the pharmacy network 8a may be different protocols. In some embodiments, the protocol used between correlation system 2 and the pharmacy network 8a may be, comply with, and/or correspond to at least a portion of a National Council for Prescription Drugs Programs (NCPDP) standard, format, or protocol. In some embodiments, the protocol used between correlation system 2 and the pharmacy network 8a may be, comply with, and/or correspond to at least a portion of or another standard or format used by and/or within pharmacy networks other than an NCPDP standard to electronically convey electronic pharmacy data and events. In some embodiments, the protocol used between correlation system 2 and the EMR network 8b may be, comply with, and/or correspond to at least a portion of a Health Level Seven International (HL7) standard, format or protocol. In some embodiments, the protocol used between correlation system 2 and the EMR network 8b may be, comply with, and/or correspond to at least a portion of another standard or format different from the HL7 standard and used by and/or within a type of health care organization (e.g., a hospital, a medical practice, an EMR data warehouse, etc.) to electronically convey information and data. In some embodiments, the protocol used by another health organization's network (e.g., one of the networks 8c-8n) may be, comply with, and/or correspond to at least a portion of an HL7 standard, but may be different from the protocol used by the EMR network 8*b*.

Figure 2:
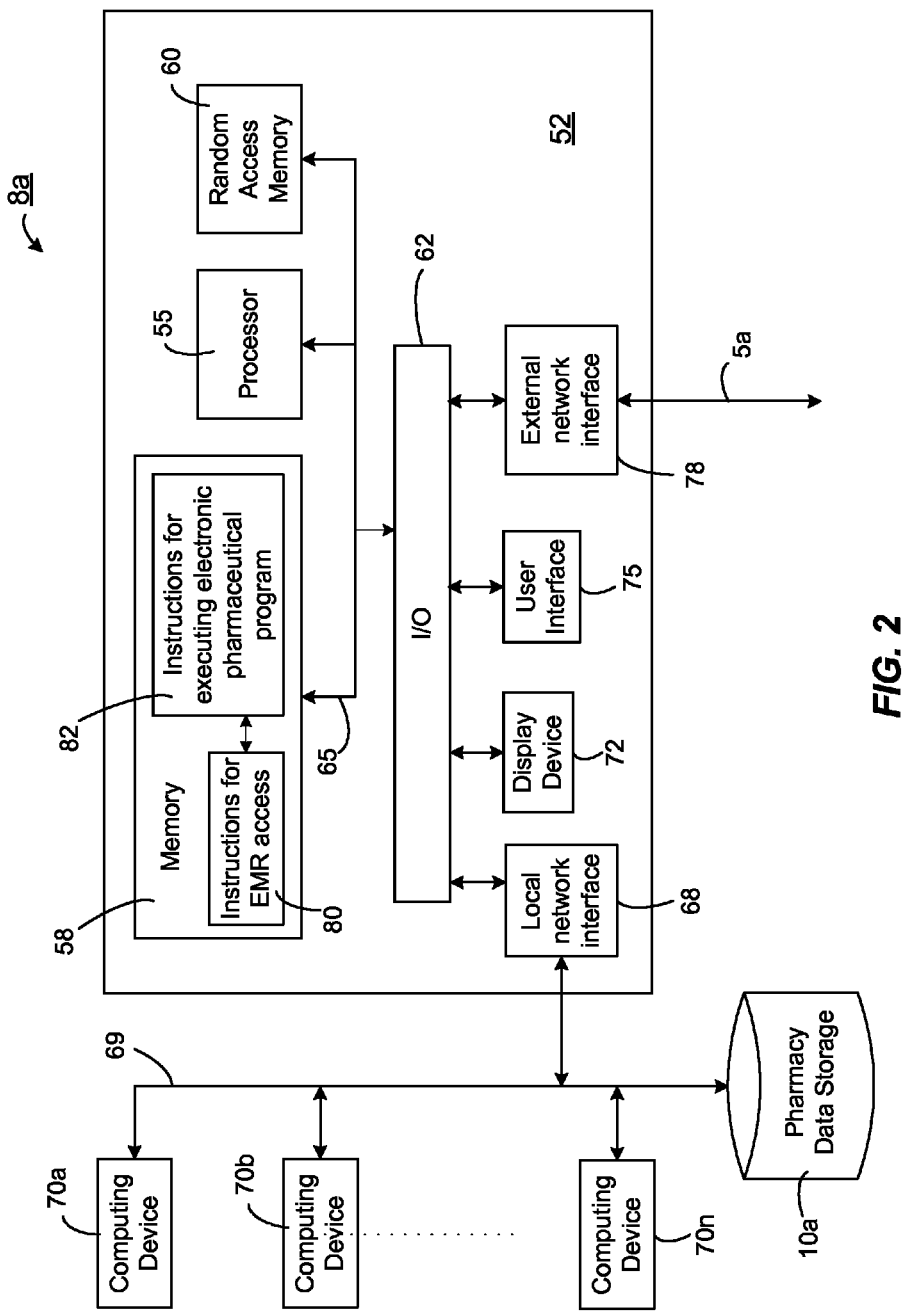
FIG. 2 illustrates an example of an expanded block diagram of the pharmacy network shown in FIG. 1, including a simplified block diagram of a computing device included in the pharmacy network.

FIG. 2 illustrates an example of an expanded block diagram of the pharmacy network 8*a* or system for executing one or more electronic pharmacy programs that require access to one or more electronic medical records shown in FIG. 1, including a simplified block diagram of an example computing device or computer 52 included in the pharmacy network 8*a* to illustrate the principles of the instant disclosure. However, such principles may apply equally to other electronic devices, including, but not limited to, cellular telephones, smart phones, tablets or other wireless devices, personal digital assistants, media players, appliances, set top boxes, and automotive dashboard electronics, to name a few. Although the discussion herein refers to a single computer 52 for clarity purposes, the principles may be easily applied to more than one computer 52, such as a network of computers 52 that appears as a single logical computing device 52.

The computer 52 may include a processor 55 (may be called a controller, microcontroller or a microprocessor, in some embodiments) for executing computer-executable instructions, a program memory 58 for permanently storing data related to the computer-executable instructions, a random-access memory (RAM) 60 for temporarily storing data related to the computer-executable instructions, and an input/output (I/O) circuit 62, all of which may be interconnected via an address/data bus 65. As used herein, the terms "computer-executable instructions," "computer executable instructions," and "instructions" are used interchangeably.

In some embodiments, the computer or computing device 52 may be communicatively connected to other entities within the pharmacy network 8*a* via a local network interface 68. For example, the computing device 52 may be communicatively and/or operatively connected to one or more other computing devices 70*a*-70*n* via the link 69, using, for example, wired and/or wireless Ethernet technology, single or multistage networking technology, or any suitable networking technology, in a manner such as previously discussed. In an embodiment, the link 69 includes multiple links that are communicatively connected and/or networked. In an embodiment, the link 69 includes the link 15*a* of FIG. 1, and as such, the computing device 52 may also be coupled to the pharmacy data storage entity 10*a* via the link 69. Many types of links are known in the art of networking and may be contemplated for use with the link 69. Other entities, although not illustrated in FIG. 2, may also be included in the pharmacy network 8*a* and may be communicatively connected by the link 69, such as, for example, a web server, a printer, a filling machine or entity, and other entities that may be utilized by the pharmacy enterprise.

In some embodiments, the pharmacy data storage entity 10*a* may not be networked to the computing device 52 as illustrated in FIG. 2, but instead the pharmacy data storage entity 10*a* may be incorporated into the computing device 52 and/or into one or more computing devices 70*a*-70*n* of the pharmacy network 8*a*. For example, the pharmacy data storage entity 10*a* may be included in the computing device 52 and, as such, the pharmacy data storage entity 10*a* may be locally accessible to the processor 55 and to other elements of the computing device 52 via the I/O circuit 62. In another example, the pharmacy data storage entity 10*a* may be a logical entity whose may be distributed across more than one computing device 52, 70*a*-70*n* of the pharmacy network 8*a* using cloud computing techniques or any other suitable distributed data storage techniques.

It should be appreciated that although only one processor 55 is shown, the computer 52 may include multiple processors 55. Similarly, the memory of the computer 52 may include multiple RAMs (Random Access Memories) 60, multiple program memories 58, and/or multiple data storage entities 12. The RAM(s) 60, program memories 58, and/or the pharmacy data storage entity 10*a* may be implemented as one or more semiconductor memories, magnetically readable memories, optically readable memories, and/or other tangible, non-transitory computer-readable storage media, for example.

Additionally, although the I/O circuit 62 is shown as a single block, it should be appreciated that the I/O circuit 62 may include a number of different types of I/O circuits. For example, a first I/O circuit may correspond to a display device 72, and the first or a second I/O circuit may correspond to a user interface 75. The user interface 75 may be, for example, a keyboard, a mouse, a touch screen, a voice activation device, or any other known user interface device. In some embodiments, the display device 72 and the user interface 75 may be jointly incorporated in a single physical device. In some embodiments, the display device 72 and/or the user interface 75 may be omitted from the computing device 52. The computing device 52 may also include other elements common to general purpose computing devices (not shown).

The computing device or computer 52 may be communicatively connected to other networks 8*b*-8*n* that are external to the pharmacy network 8*a* via an external network interface 78 and the link 5*a*. The link 5*a* may be an Ethernet connection, an IP (Internet Protocol) connection or the like; and the link 5*a* may be a wired, wireless, or multi-stage connection. Many types of links are known in the art of networking and may be used in conjunction with the computing device 52. In some embodiments, the external network interface 78 and the local network interface 68 may be incorporated into a single network interface (not shown).

The computing device 52 may include computer-executable electronic medical record (EMR) access instructions 80 stored on a tangible, non-transitory computer-readable storage medium, such as on the memory 58 or on some other suitable memory. The EMR access instructions 80 may include one or more sets of computer-executable instructions for accessing electronic medical records (EMRs). The EMR access instructions 80 may be executable by one or more processors 55 to access one or more EMRs to obtain desired data.

Computer-executable instructions 82 that are executable by one or more processors 55 to execute an electronic pharmacy program may also be stored in the memory 58 of the computing device 52, as illustrated in FIG. 2, or may be stored in some other suitable memory. The electronic pharmacy program instructions 82 may be executed by one or more processors 55 to perform a pharmacy function such as filling a prescription; billing a prescription; counseling or dispensing advice with regard to proper or desired use of the prescription; counseling or dispensing advice with regard to possible adverse events with respect to the prescription; providing disease state management; monitoring drug therapy; and/or any other activity that may be performed at a pharmacy location of the pharmacy network 102. Data that is accessed via an EMR may be required for an execution of at least part of an electronic pharmacy program. For example, the electronic pharmacy program may be a pharmacy billing program that requires an electronic check of whether or not the patient is eligible for a local, state or federal government program (e.g., United States federal government's 340B Drug Pricing Program (as used herein, "340B"), and other programs) so that accurate charges may be presented on the bill. In another example, the electronic pharmacy program may operate in conjunction with a clinical aftercare program, a disease state management program, or a medication therapy management program in which the patient is participating, where at least a portion of the program(s) requires current vital signs data or other disease state diagnoses of a patient. Typically, but not necessarily, the execution of at least a part of the electronic pharmacy program may utilize or be based on data included in a pharmaceutical or pharmacy record of a patient, such as an identity of the patient, a disease state, a date of service, or any other data that may be included in the patient's pharmaceutical or pharmacy record. Other examples of electronic pharmacy programs are possible and may operate in conjunction with the principles of the present disclosure.

The instructions for EMR access 80 and the instructions for executing one or more electronic pharmacy programs may be stored in the memory 58 and may be executable by the processor 55 of the computing device 52, as illustrated in FIG. 2. In some embodiments, however, the instructions for accessing electronic medical records 80 may be stored on and executed by the computing device 52, while the instructions for executing the electronic pharmacy program 82 that requires the EMR data may be stored on and executed by a different computing device (e.g., at least one of the computing devices 70a-70n). In the latter embodiment, the electronic pharmacy program 82 may be communicatively coupled to the instructions for accessing electronic medical records 80. For example, the electronic pharmacy program instructions 82 may invoke the EMR access instructions 80 via a function call, a macro, a message exchange, or any suitable interface.

It is noted that although FIG. 2 illustrates an expanded block diagram of the computing device 52, any of the elements shown as being included in the computing device 52 may be included in each of the computing devices 70a-70n of the pharmacy network 8a. In some embodiments of the system 8a, each of the computing devices 70a-70n and 52 may be identically configured. In other embodiments, at least two of the computing devices 70a-70n and 52 may be differently configured. For example, a single computing device 52 may include the external network interface 78 for all computing devices 52, 70a-70n of the pharmacy network 8a, and thus, may serve as a gateway between the pharmacy network 8a and external networks 8b-8n. In another example, at least two of the computing devices 52, 70a-70n may be configured with their own respective external network interface 78 to the external networks 8b-8n. In an embodiment, only one computing device (e.g., computing device 52) of the system 8a may be configured with the instructions 80 for EMR access, and other computing devices having electronic pharmacy programs 82 executing thereon may interface with the instructions 80 when EMR data access is required. In other embodiments, at least two of the computing devices 52, 70a-70n may be configured with the instructions 80 to execute locally when EMR data access is required by a co-resident electronic pharmacy program 82. Of course, the above examples are illustrative only, and other configurations of the system 8a and configurations of computing devices 52, 70-7n included therein may be possible.

FIGS. 3A-3D include example process flows used in correlating or associating electronic pharmacy data and electronic medical records between a pharmacy network 102, a correlation or association system 105, and an EMR network 108. In an embodiment, the process flows shown in FIGS. 3A-3D may operate in conjunction with embodiments of the system 1 of FIG. 1. For example, the pharmacy network 102 may be the pharmacy network 8a, the correlation or association system 105 may be the correlation system 2, and the EMR network 108 may be the EMR network 8b of FIG. 1. In an embodiment, each of the inputs and outputs to the pharmacy network 102, the correlation or association system 105, and the EMR network 108a are processed by one or more computing devices included respectively therein executing computer-executable instructions. For illustrative but non-limiting purposes, however, the process flows shown in FIGS. 3A-3D are described below in conjunction with elements of FIGS. 1 and 2.

With further respect to FIGS. 3A-3D, any communication or messaging between the correlation system 105 and the EMR network 108 or between the correlation system 105 and the pharmacy network 102 may be acknowledged and may include error scenario processing, although, for clarity purposes, such acknowledgements and error leg scenario processing communications are not shown in FIGS. 3A-3D. For example, although not shown in FIG. 3A, a reception of an EMR network registration 110 at the correlation system 105 may cause the correlation system 105 to return an acknowledgement, and if the EMR network 108 does not receive the expected acknowledgement within a defined time window, the EMR network 108 may proceed with error leg processing to resolve the situation. In another example, if the correlation system 105 receives a message or communication of an unexpected format or including unexpected data values from the pharmacy network 102, the correlation system 105 may proceed with error leg processing to resolve the situation.

Figure 3A:
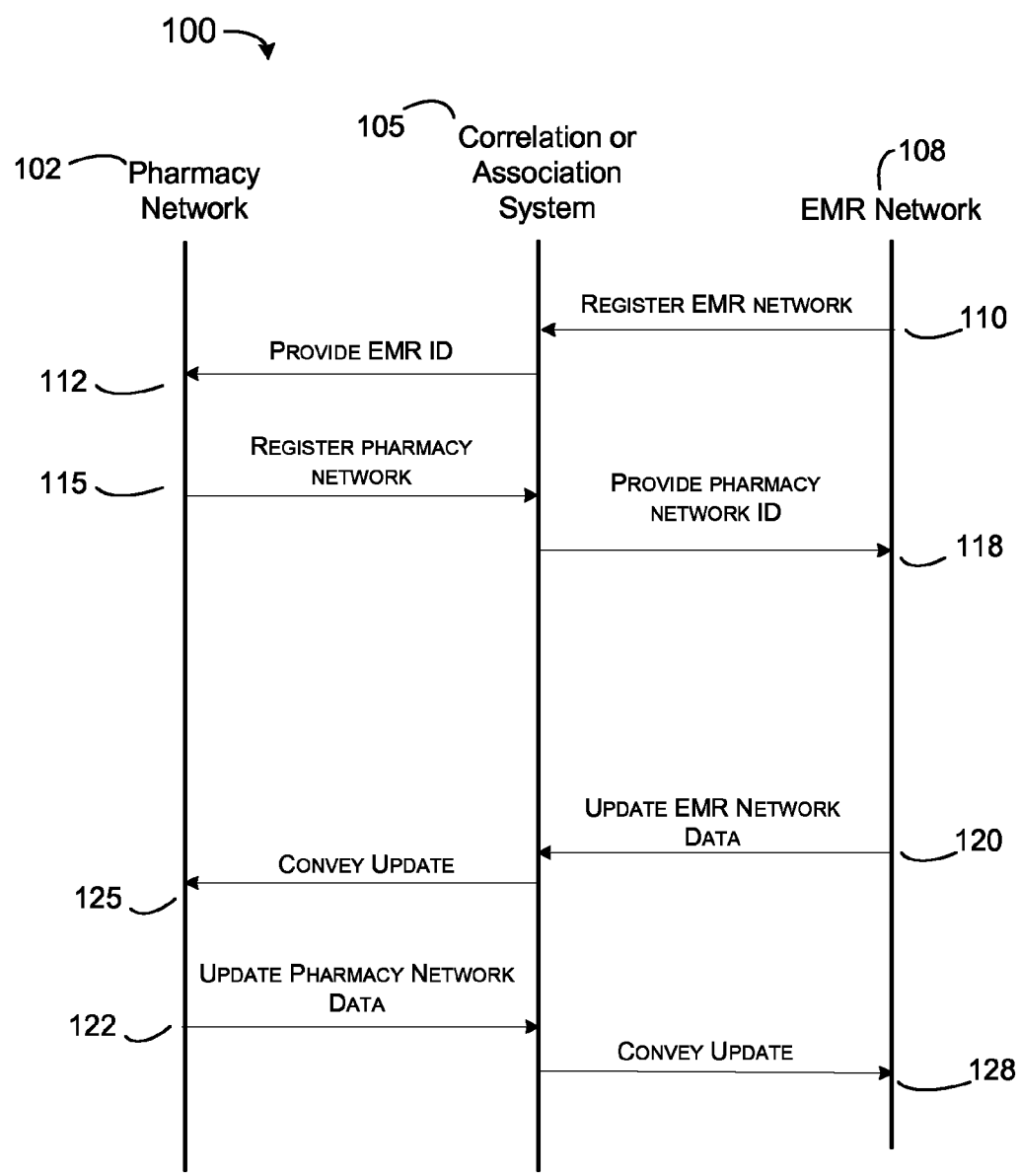

FIG. 3A illustrates an example process flow 100 for registering networks and creating network profiles at the correlation or association system 105. An EMR network 108 may register 110 with the correlation or association system 105. The correlation system 105 may register the EMR network 108 by creating a profile corresponding to the EMR network 108. The EMR network profile may include at least one of: a name of the EMR network 108, a network or system identification (ID) of the EMR network 108, a name for each location or facility included in the EMR network 108 (or computing device corresponding to each location or facility), a location code, identification or ID for the each location or facility, and/or parameters corresponding to characteristics of each location. The system identification of the EMR network 108 typically, but not necessarily, may be unique within the range of system or network identifications managed by the correlation system 105. Characteristics of each location of the EMR network 108 may include, for example, an indication of whether each location is qualified for any federal or state governmental programs, such as the United States federal government's 340B Drug Pricing Program.

The EMR network profile may further include an indication of a database access mechanism, communication protocol, and/or messaging format that the EMR network 108 utilizes. For example, the EMR network profile may indicate one or more HL7 protocols or formats with which the EMR network 108 compatible or that the EMR network 108 supports. The EMR network profile corresponding to the EMR network 108 may additionally include contact information for one or more representatives of the EMR network 108, and other administrative information. The created EMR network profile may be stored in the correlation system 105, for example, in the data storage entity 12.

In some embodiments, rather than the correlation system 105 creating the profile of the EMR network 108, the EMR network 108 may send its profile or selected portions thereof to the correlation system 105 during the registration process 110, and the correlation system 105 may store the received profile or selected portions thereof. The correlation system

105 may notify 112 the pharmacy network 102 of the assigned EMR network ID and of any other desired data corresponding to the registered EMR network 108.

In a similar manner, a pharmacy network 102 may register 115 with the correlation system 105. The correlation system 105 may register the pharmacy network 102 by creating a profile corresponding to the pharmacy network 102. The pharmacy network profile may include at least one of: a name of the pharmacy network 102, a system identification of ID of the pharmacy network 102, a name for each location or facility included in the pharmacy network 102 (or computing device corresponding to each location or facility), a location code, identification or ID for the each location or facility, and/or parameters corresponding to characteristics of each location. The system identification of the pharmacy network 102 typically, but not necessarily, may be unique within the range of system or network identifications managed by the correlation system 105. Characteristics of each location included in the pharmacy network 102 may include, for example, an indication of whether each location is qualified for any federal or state governmental programs, such as the United States federal government's 340B Drug Pricing Program. The pharmacy network profile may include an indication of a database access mechanism, communication protocol, and/or messaging format that the pharmacy network 102 utilizes or supports. For example, the pharmacy network profile may indicate one or more NCPDP standards with which the database access mechanism and/or the communication protocol utilized by the pharmacy network 102 is compatible.

The pharmacy network profile corresponding to the pharmacy network 102 may additionally include contact information for one or more representatives of the pharmacy network 102. The created pharmacy network profile may be stored in the correlation system 105, for example, in the data storage entity 12.

In some embodiments, rather than the correlation system 105 creating the profile of the pharmacy network 102, the pharmacy network 102 may send its profile or selected portions thereof to the correlation system 105 during the registration process 115, and the correlation system 105 may store the received profile or portions thereof. The correlation system 105 may notify 118 the EMR network 108 of the pharmacy network ID and of any other desired data corresponding to the pharmacy network 102.

In some embodiments, the profile of an EMR network 108 and/or the profile of the pharmacy network 102 may be independently updated 120, 122 based on respective network changes. The data included in the updates 120, 122 may reflect the respective network changes. In some embodiments, the update to the EMR network profile 120 and/or the update to the pharmacy network profile 122 may be generated in conjunction with a trigger event that occurs. For example, an update 120 may be sent to the correlation system 105 if the name of the EMR network 108 changes. In another example, when the pharmacy network 102 adds an additional pharmacy location, an update 122 may be sent to the correlation system 105. In some embodiments, at least some portion of the updated information 120, 122 may be respectively communicated 125, 128 by the correlation system 105 to the other network 102, 108.

Note that the communications 110-118 of FIG. 3A may be performed in any suitable order. For example, the pharmacy network 102 may register 115 with the correlation system 105 before the EMR network 110 registers. In some embodiments, more than one EMR or other network 108 may register (e.g., more than one of the networks 8b, 8c, ..., 8n), so that the flows 110 and 112 are repeated for each registering EMR or other network. In some embodiments, the pharmacy network 102 may send several updates 122 while the EMR network 108 does not send any updates.

Figure 3B:
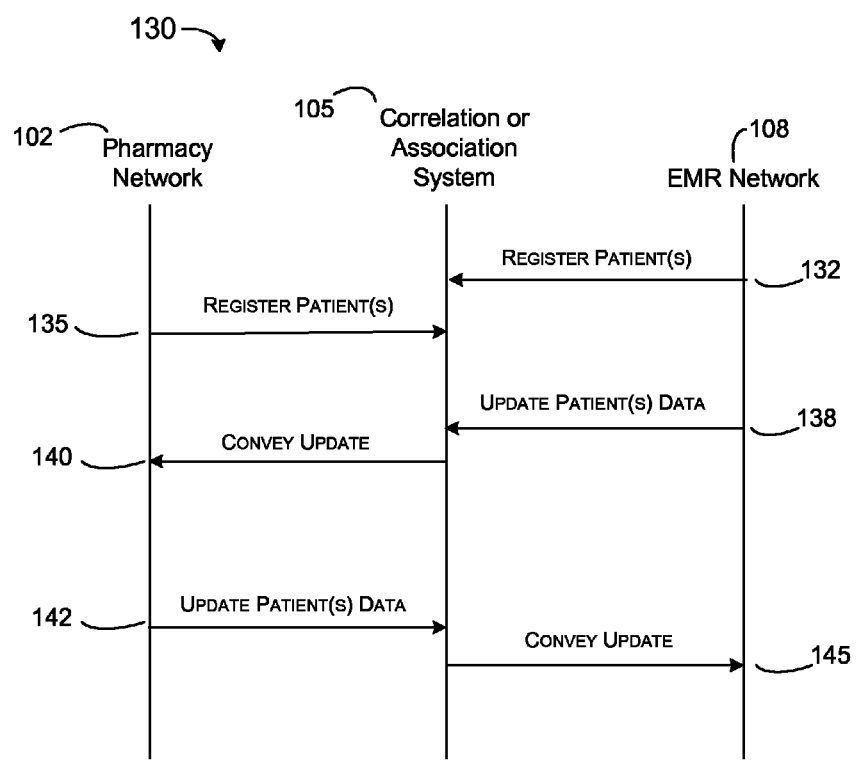

FIG. 3B illustrates an example process flow 130 for registering a patient with the correlation or association system 105. An EMR network or EMR computing network 108 may send a patient registration 132 to the correlation or association system 105. Upon reception of the patient registration 132, the correlation system 105 may register the patient by creating a patient data file corresponding to the patient, and storing the patient data file in a data storage location that is accessible to the correlation system 105, such as the data storage entity 12.

The patient data file may include at least one of: a name of the EMR network 108 from which the patient registration 132 was received; a system identification of ID of the EMR network 108 from which the patient registration 132 was received; a patient name, address, date of birth, contact information, and other personal information; a patient medical record number or identifier; and other desired data. The contents of the patient data file may be based, at least in part, on one or more EMRs that correspond to the patient and that are stored in the EMR network 108. In an embodiment, at least a portion of the contents of the one or more EMRs that correspond to the patient may be stored in the patient data file accessible to the correlation system 105. For example, at least a portion of records of physician visits, diagnoses, orders, consultations, symptoms, and the like may be stored in the patient data file. In an embodiment, the information from the one or more EMRs may be stored in the patient data file using a format utilized by the EMR network 108, such as a format that is compatible with an HL7 standard.

In some embodiments, the patient data file accessible to the correlation system 105 is a single, logical patient data file that is created for a particular patient. The logical patient data file may store aggregated data or information received from more than one registered pharmacy network, EMR network, and/or other networks. In some embodiments, multiple different logical patient data files corresponding to a particular patient may be created, one for each different registered network, and these multiple patient data files corresponding to the particular patient may be linked.

In some embodiments, the patient registration 132 may be sent in conjunction with a trigger event that occurs at the EMR network 108. A trigger event may include, for example, a patient encounter. For example, a previously non-registered patient may receive health care services. As a result of received health care services, an electronic medical record corresponding to the patient may be created or updated, and the patient may be registered at the correlation system 105 after the patient encounter during which the health care services were received. In these embodiments, the patient registration 132 may also include data corresponding to patient encounter, such as the location at which the encounter occurred, the date of the encounter, parameters corresponding to characteristics of the location (such as those previously discussed with respect to the network registration 110 or other characteristics), and/or other data. In an embodiment, the patient registration 132 may include data from the EMR corresponding to the patient.

At the correlation system 105, the patient data file may be stored, for example, in the data storage entity 12. If, upon reception of the patient registration 132, the correlation system 105 determines that the patient has already been previously registered (e.g., a patient data file already exists at the correlation system 105 e.g., resulting from a previous registration received from the EMR network 108, the pharmacy network 102, or some other network), additional or updated information corresponding to the patient and included in the registration 132 may merely be added to or changed in the existing patient data file. For example, the identification of the EMR network 108 may be added to the patient data file.

In some embodiments, rather than the correlation system 105 creating the patient data file, the EMR network 108 may send a patient's data file or selected portions thereof to the correlation system 105 during the registration process of the EMR network 108 (e.g., the EMR network registration 110), and the correlation system 105 may store the received patient data file or selected portions thereof. In some embodiments, the EMR 108 may send a batch or bulk patient registration 132 to the correlation system 105, for example, when the EMR network 108 initially registers 110 with the correlation system 105, when the EMR network 108 adds a new location or group of patients, when a user request (e.g., a user request initiated at the EMR network 108, the correlation system 105 or the pharmacy network 102) for a batch registration is received, or during any desired or suitable scenario. The batch or bulk patient registration 132 may include multiple patient data files and/or data corresponding to respective multiple patients and their EMRs. In some embodiments, the bulk or batch patient registration 132 may be split across multiple transmissions from the EMR network 108 to the correlation system 105.

In a similar manner, a pharmacy network 102 may register 135 a patient with the correlation system 105. Upon reception of the registration 135, the correlation system 105 may register 135 the patient by creating a patient data file corresponding to the patient. The patient data file may include at least one of: a name of the pharmacy network 102 from which the patient registration 135 was received; a system identification of ID of the pharmacy network 102 from which the patient registration 135 was received; a patient name, address, date of birth, contact information, and other such personal information; a patient pharmaceutical or pharmacy record number or identifier; and other desired data. The patient data file may be based, at least in part, on one or more pharmaceutical or pharmacy records that correspond to the patient and that are stored in the pharmacy network 102. In an embodiment, at least a portion of the one or more pharmaceutical or pharmacy records that correspond to the patient may be stored in the patient data file accessible to the correlation system 105. For example, information from pharmacy records such as prescription fills and refills, consultation information, and the like may be stored in the patient data file. In an embodiment, the information from the one or more pharmaceutical or pharmacy records may be stored in the patient data file using a format utilized by the pharmacy network 102, such as a format that is compatible with an NCPDP standard.

In some embodiments, the patient registration 135 may be sent in conjunction with a trigger event that occurs at the pharmacy network 102 and that typically, but not necessarily, corresponds to a pharmaceutical or pharmacy record corresponding to the patient. A trigger event may include, for example, an encounter with a patient or with the patient's representative. For example, a representative of a previously non-registered patient (e.g., a parent of a minor child) may request to fill a prescription at a location within the pharmacy network 102, and a pharmaceutical or pharmacy record included in the pharmacy network 102 may be created or updated corresponding to the fill. The patient may be registered at the correlation system 105 after the pharmacy network encounter during which the prescription was filled. In these embodiments, the patient registration 135 may also include data corresponding to encounter, such as the location at which the encounter occurred, the date of the encounter, parameters corresponding to characteristics of the location (such as those previously discussed with respect to the pharmacy network registration 115 or other characteristics), and/or other data. In an embodiment, the patient registration 135 may include data from the pharmaceutical or pharmacy record corresponding to the patient.

At the correlation system 105, the patient data file may be stored, for example, in the data storage entity 12. If, upon reception of the patient registration 135, the correlation system 105 determines that the patient has already been previously registered (e.g., a patient data file already exists, e.g., resulting from a previous registration received from the EMR network 108, the pharmacy network 102, or some other network), additional or updated information corresponding to the patient included in the patient registration 135 may merely be added to the existing patient data file at the correlation system 105. For example, the identification of the pharmacy network 102 may be added to or changed in the patient data file.

In some embodiments, rather than the correlation system 105 creating the patient data file, the pharmacy network 102 may send the patient data file or selected portions thereof to the correlation system 105 during the registration process of the pharmacy network 102 (e.g., the pharmacy network registration 115). The correlation system 105 may store the received patient data file or selected portions thereof.

In some embodiments, the pharmacy network 102 may send a batch or bulk patient registration 135 to the correlation system 105. For example, a batch or bulk patient registration 135 may be transmitted when the pharmacy network 102 initially registers with the correlation system 105, when the pharmacy network 102 adds a new location or group of patients, when a user requests a bulk registration (e.g., a user of the pharmacy network 102, the correlation system 2 or the EMR network 108 requests a batch or bulk patient registration 135 to be sent), or during any desired or suitable situation. The batch or bulk patient registration 135 may include multiple patient data files and/or data corresponding to respective multiple patients and their pharmaceutical or pharmacy records. In some embodiments, the bulk or batch patient registration 135 may be split across multiple transmissions from the pharmacy network 102 to the correlation system 105.

In some embodiments, a patient data file (or multiple patient data files) stored at the correlation system 105 may be updated 138 by the EMR network 108 based on changes made at the EMR network 108. In some embodiments, the patient update 138 may be sent from the EMR network 108 to the correlation system 105 in conjunction with a trigger event that occurs at the EMR network 108. For example, an update 138 may be sent to the correlation system 105 after a patient encounter occurs. In another example, if a patient changes his or her residence and the patient's EMR is updated with the new address, the EMR network 108 may send an update 138 to the correlation system 105 reflecting the change of address so that the correlation system may update the stored patient data file(s). In yet another example, a patient update 138 may be generated and transmitted based on a user request initiated at the EMR network 108, the correlation system 105, the pharmacy network 102, or another network. Generally, any scenario that occurs at the EMR network 108 that requires an update to data that is stored in the patient data file at the correlation system 105 may cause the EMR network 108 to generate and transmit an update 138. In some embodiments, at least some portion of the updated information 138 may be respectively communicated 140 by the correlation system 105 to the other pharmacy network 102.

In some embodiments, the EMR network 108 may send a batch or bulk patient update 138 to the correlation system 105. The batch or bulk patient update 138 may include updated data from multiple patient data files and/or updated data corresponding to respective multiple patients and their EMRs. In some embodiments, the batch or bulk patient update 138 may be split across multiple transmissions from the EMR network 108 to the correlation system 105.

In some embodiments, the content of a batch or bulk patient update 138 may be selected or filtered based on a selection parameter. The selection parameter may be indicated by a user (e.g., by an electronic user of the pharmacy network 102, of the correlation system 105, of the EMR network 108, or of some other network). The selection parameter may filter patient data to be included in the batch patient update 138 by selectable criteria such as a number of EMRs, a number of patients, a range of dates, patient program ineligibility or eligibility, a particular health care provider, or any other data or characteristic of data that may be included in or associated with a patient's data file and/or EMR. In some embodiments, more than one selection parameter may be used to filter the contents of the batch or bulk patient update 138.

In some embodiments, the batch or bulk patient update 138 may be transmitted from the EMR network 108 to the correlation system 105 at pre-determined intervals, such as hourly, daily, weekly or at any desired or suitable interval. The interval may be selectable and/or adjustable. In some embodiments, the batch or bulk patient update 138 may be sent as a result of a user request, such as a request of an electronic user initiated at the pharmacy network 102, the correlation system 105, the EMR network 108, or some other network.

In some embodiments, a patient data file (or multiple patient data files) stored at the correlation system 105 may be updated 142 by the pharmacy network 102 based on changes made at the pharmacy network 102. In some embodiments, the patient update 142 may be sent from the pharmacy network 102 to the correlation system 105 in conjunction with a trigger event that occurs at the pharmacy network 102 that typically, but not necessarily, corresponds to a pharmaceutical or pharmacy record of the patient. For example, an update 142 may be sent to the correlation system 105 after a patient-related encounter occurs, such as when a parent of a minor patient picks up a filled prescription, or when a patient orders and pays for a prescription on-line. In another example, if a patient of a pharmacy network 102 changes a primary pharmacy location at which he or she receives services, the pharmacy network 102 may send an update 142 to the correlation system 105. In yet another example, a patient update 142 may be generated and transmitted based on a user request initiated at the EMR network 108, the correlation system 105, the pharmacy network 102, or another network. Generally, any scenario occurring at the pharmacy network 102 that requires an update to the patient data file at the correlation system 105 may cause the pharmacy network 102 to generate and transmit an update 142. In some embodiments, at least some portion of the updated information 142 may be communicated 145 by the correlation system 105 to the EMR network 108.

In some embodiments, the pharmacy network 102 may send a batch or bulk patient update 142 to the correlation system 105. The batch or bulk patient update 142 may include updated data from multiple patient data files and/or updated data corresponding to respective multiple patients and their pharmaceutical or pharmacy records. In some embodiments, the batch or bulk patient update 142 may be split across multiple transmissions from the pharmacy network 102 to the correlation system 105.

In some embodiments, the content of a batch or bulk patient update 142 may be selected or filtered based on a selection parameter. The selection parameter may be indicated by a user (e.g., by an electronic user of the pharmacy network 102, of the correlation system 105, of the EMR network 108, or of some other network). The selection parameter may filter patient data to be included in the batch patient update 142 by selectable criteria such as a number of pharmaceutical or pharmacy records, a number of patients, a range of dates, patient program ineligibility or eligibility status, a particular pharmacy location, or any other data or characteristic of data that may be included in or associated with a patient's data file and/or pharmaceutical or pharmacy record. In some embodiments, more than one selection parameter may be used to filter the contents of the batch or bulk patient update 142.

In some embodiments, the batch or bulk patient update 142 may be transmitted from the pharmacy network 102 to the correlation system 105 at pre-determined intervals, such as hourly, daily, weekly or at any desired or suitable interval. The interval may be selectable and/or adjustable. In some embodiments, the batch or bulk patient update 142 may be sent as a result of a user request, such as a request initiated by an electronic user of the pharmacy network 102, the correlation system 105, the EMR network 108, or some other network.

Note that the communications 132-145 of FIG. 3B may be performed in any suitable order. For example, a patient may be registered by the pharmacy network 102 before the patient is registered by the EMR network 108. In another example, a patient may be registered 135 by the pharmacy network 102 and the patient data file may be updated 142 several times by the pharmacy network 102 before the EMR network initially registers the patient 132. Other orders of the communication flows 132-145 may be possible.

FIG. 3C illustrates an example process flow 150 for correlating pharmacy data and electronic medical records. The illustrated process flow 150 includes two sets of example communication or message exchanges 152, 172 that may occur in any order, or may both occur during an overlapping interval of time. In the first example message exchange 152, the EMR network 108 may require data that is available at the pharmacy network 102. As previously discussed, however, the EMR network 108 and the pharmacy network 102 may be each separately secured. Furthermore, the EMR network 108 and the pharmacy network 102 may each access patient data maintained therein (e.g., electronic medical records and pharmaceutical or pharmacy records, respectively) using different access mechanisms. Still further, the EMR network 108 and the pharmacy network 102 may each communicate with other networks using different protocols. For example, the EMR network 108 database access mechanism and/or the EMR network 108 communication protocol may be based, at least partially, on an HL7 format, whereas the pharmacy network 102 database access mechanism and/or the pharmacy network 102 communication protocol may be based, at least partially, on an NCPDP standard.

Accordingly, to obtain the required patient data from the pharmacy network 102, the EMR network 108 may send a query or request 155 to the correlation system 105. The query 155 may include a request for patient-related and/or network-related data that is available from the pharmacy network 102 but is not available from the EMR network 108. Generally, queries 155 may include one or more requests for any data that is available from a network different from the originating network (e.g., a "target" or "destination" network such as the pharmacy network 102 and/or another network 8c-8n). For example, the query 155 may include a request for patient data included in a patient's pharmaceutical or pharmacy record. In some embodiments, a query 155 may additionally or alternatively include a request for data that is specific to the destination network. For example, the query 155 may include a request for data corresponding to a particular pharmacy location included in the pharmacy network 102. The query 155 may include an indication of the target or destination network from which the desired data may be obtained, but this inclusion of the target or destination network indication is optional.

The correlation system 105 may receive the query from the originating network (e.g., the EMR network 108), and may determine the network from which the desired patient data may be obtained. For example, the correlation system 105 may determine the destination network based on the contents of the query and/or based on contents of a corresponding patient data file. Additionally or alternatively, the correlation system 105 may determine the destination network based on network information that is accessible to the correlation system 105. In an embodiment, the correlation system 105 may access one or more databases stored at the data storage entity 12 to determine the destination network.

Based on the information stored at or accessible to the correlation system 105 (e.g., stored in the data storage entity 12), the correlation system 105 may determine a format that is compatible with the destination network, and may convert 158 the query 155 into the determined format. For instance, in the example illustrated in FIG. 3C, the correlation system 105 may determine the format that is compatible with the pharmacy network 102 based on a network profile of the pharmacy network 102, and may convert 158 the query 155 into the determined format. In an embodiment, the correlation system 105 may convert 158 the query 155 by wrapping the query 155 in a wrapper that is compatible with the format compatible with the pharmacy network 102. The converted query 160 may be transmitted from the correlation system 105 to the destination network (e.g., to the pharmacy network 102).

After the destination network (e.g., the pharmacy network 102) has received the converted query 160, the destination network may generate a response 162 that includes the desired data. The response 162 may include any data that is included or stored in an EMR corresponding to the query 155, in an embodiment. The response 162 may be transmitted back to the correlation system 105, and the correlation system 105 may convert 165 the response 162 into a format that is compatible with the originating network (e.g., the EMR network 108). For instance, in the example illustrated in FIG. 3C, the correlation system 105 may determine the format that is compatible with the EMR network 108 based on a network profile of the EMR network 108 or based on data corresponding to the query 155, and may convert 165 the response 162 into the determined format. In an embodiment, the correlation system 105 converts 165 the response 162 by wrapping the response 162 in a wrapper that is compatible with the format compatible with the EMR network 108. The converted response 168 may be transmitted from the correlation system 105 to the originating network (e.g., to the EMR network 108), and the originating network may then proceed with its processing of the desired data included in the converted response 168.

With further regard to FIG. 3C, during the second example message exchange 172, the origination and the destination network roles may be reversed. In particular, the pharmacy network 102 may require data that is available at the EMR network 108. Accordingly, the pharmacy network 102 may send a query or request 175 to the correlation system 105. The query 175 may include a request for patient-related data and/or network-related data that is available from the EMR network 108 but is not available from the pharmacy network 102. Generally, queries 175 may include one or more requests for any patient-related data that is available on a network different from the originating network. For example, the query 175 may include a request for patient data that is included in a patient's electronic medical record. In some embodiments, a query 175 may additionally or alternatively include a request for network-related data that is specific to the destination network (e.g., data corresponding to EMR network 108). In some embodiments, the query 175 may include a request for an indication of whether or not a patient is eligible for a particular government drug program, e.g., a United States federal government 340B Drug Pricing Program. For example, the query 175 may include a request for information pertaining to patient visits to or encounters with qualified 340B program locations, and/or may include a request for time elapsed since the last patient visit to or encounter with a qualified 340B program location. The query 175 may include an indication of the target or destination network (e.g., the EMR network 108 and/or another network 8c-8n) from which the desired data may be obtained, but the inclusion of the indication of the destination network in the query 175 is optional.

The pharmacy network 102 may initiate the query when an electronic pharmacy program executing in the pharmacy network 102 requires information from the EMR network 108, such as from a particular patient's EMR. In some embodiments, the pharmacy network 102 may initiate the query 175 based on a pharmaceutical or pharmacy record of the particular patient (e.g., a pharmaceutical or pharmacy record stored in the pharmacy data storage 10a of the pharmacy network 8a). For example, the electronic pharmacy program may be a pharmacy billing program that generates a bill for a prescription at least partially based on the particular patient's pharmaceutical or pharmacy record. During the execution of the pharmacy billing program, an electronic check of whether or not the patient is eligible for a local, state or federal government program may be required to properly assess charges, and the query 175 may be generated and caused to be transmitted. For example, to determine whether or not a patient is eligible for the U.S. federal 340B program, the query 175 may request information pertaining to patient visits to or encounters with qualified 340B program locations, and/or the query may request information pertaining to elapsed time since the last patient visit to or encounter with a qualified 340B program location. Other examples of electronic pharmacy programs that execute at least part of a pharmaceutical or pharmacy function and cause the pharmacy network 102 to generate or initiate a query 175 for information from another network may be possible.

The correlation system 105 may receive the query from the pharmacy network 102 and may determine the network from which the desired patient data may be obtained, i.e., the destination network. For example, the correlation system 105 may make this determination based on the contents of the query 175 and/or based on a corresponding patient data file. Additionally or alternatively, the correlation system 105 may determine the destination network based on network information that is accessible to the correlation system 105. In an embodiment, the correlation system 105 may access one or more databases at the data storage entity 12 to determine the destination network.

Based on the information stored at or accessible to the correlation system 105 (e.g., stored in the data storage entity 12), the correlation system 105 may determine a format that is compatible with the destination network, and may convert 178 the query 175 into a format that is compatible with the destination network (e.g., the EMR network 108). In FIG. 3C, for example, the correlation system 105 may convert 178 the query 175 into a format that is compatible with the EMR network 108. In an embodiment, the correlation system 105 may convert 178 the query 175 by wrapping the query 175 in a wrapper that is compatible with the format compatible with the EMR network 108. The converted query 180 may be transmitted from the correlation system 105 to the destination network (e.g., to the EMR network 108).

After the destination network (e.g., the EMR network 108) has received the converted query 180, the destination network may generate a response 182 that includes the desired data. The response 182 may include any data that is included or stored in a pharmaceutical or pharmacy record corresponding to the query 175, in an embodiment. The response 182 may be transmitted back to the correlation system 105, and the correlation system 105 may convert 185 the response 182 into a format that is compatible with the originating network (in this example, the pharmacy network 102). For instance, in the example illustrated in FIG. 3C, the correlation system 105 may determine the format that is compatible with the pharmacy network 102 based on a network profile of the pharmacy network 102 or based on data corresponding to the query 175, and may convert 185 the response 182 into the determined format. In an embodiment, the correlation system 105 converts 185 the response 182 by wrapping the response 182 in a wrapper that is compatible with the format compatible with the pharmacy network 102. The converted response 188 may be transmitted from the correlation system 105 to the originating network (e.g., to the pharmacy network 102), and the originating network may then proceed with its processing of the desired data that is included in the converted response 188.

Figure 3D:
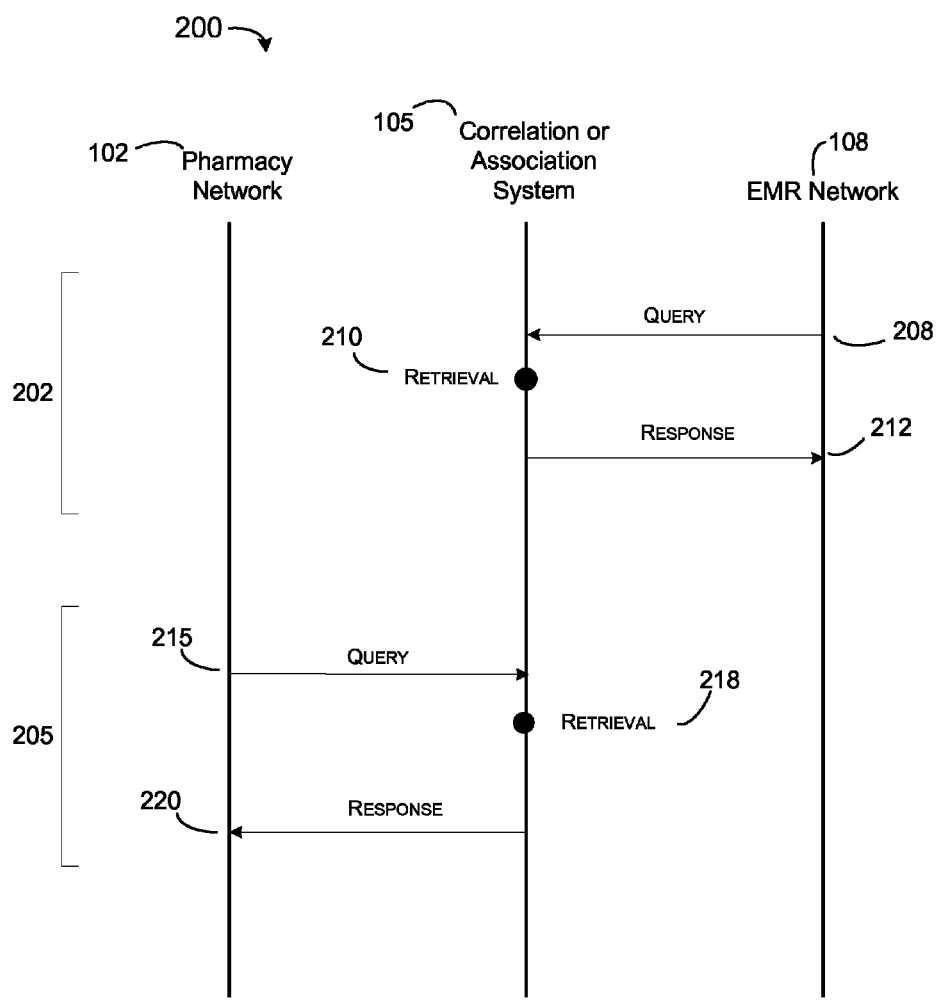

FIG. 3D illustrates an example process flow 200 for correlating pharmacy data and electronic medical records. The illustrated process flow 200 includes two sets of example communication or message exchanges 202, 205 that may occur in any order, or may both occur during an overlapping interval of time. In the first example message exchange 202, the EMR network 108 may require data that is generated by the pharmacy network 102. As previously discussed, however, the EMR network 108 and the pharmacy network 102 may be each separately secured. Furthermore, the EMR network 108 and the pharmacy network 102 may each access patient data maintained therein (e.g., electronic medical records and pharmaceutical or pharmacy records, respectively) using different access mechanisms. Still further, the EMR network 108 and the pharmacy network 102 may each communicate with other networks using different protocols. For example, the EMR network 108 database access mechanism and/or the EMR network 108 communication protocol may be based, at least partially, on an HL7 format, whereas the pharmacy network 102 database access mechanism and/or the pharmacy network 102 communication protocol may be based, at least partially, on an NCPDP standard.

Accordingly, to obtain the required patient data generated by the pharmacy network 102, the EMR network 108 may send a query 208 to the correlation system 105. The query 208 may include a request for patient-related and/or network-related data that is generated by the pharmacy network 102. Generally, queries 208 may include one or more requests for any data that is generated by a network different from the originating network (e.g., a "target" or "destination" network such as the pharmacy network 102 and/or another network 8c-8n). For example, the query 208 may include a request for patient data included in a patient's pharmaceutical or pharmacy record. In some embodiments, a query 208 may additionally or alternatively include a request for data that is specific to the destination network. For example, the query 208 may include a request for data corresponding to a particular pharmacy location included in the pharmacy network 102. The query 208 may include an indication of the target or destination network from which the desired data may be obtained, but this inclusion of the target or destination network indication is optional.

The correlation system 105 may receive the query 208 from the originating network (e.g., the EMR network 108), and may retrieve 210 the requested information from one or more patient data files accessible to the correlation system 105 (e.g., from one or more patient data files stored in the data storage entity 12). The requested information may have been previously obtained from the pharmacy network 102 during a patient registration (e.g., message 135 of FIG. 3B) or a patient record update (e.g., message 142 of FIG. 3B), and the requested information may be stored in the one or more patient data files. In an embodiment, the information obtained from the pharmacy network 102 may be stored in the one or more patient data files in a format utilized by the pharmacy network 102 (e.g., in a format compatible with an NCPDP standard). As the query 208 may be of a format other than that utilized by the pharmacy network 102, the correlation system 105 may map one or more fields of the query 208 to respective one or more fields of the one or more patient data files.

The correlation system 105 may prepare a response 212 to the query 208, including formatting the requested information into a format that is utilized by the EMR network 108, e.g., in an HL7 compatible format. The response 212 may be transmitted from the correlation system 105 to the originating network (e.g., to the EMR network 108), and the originating network may then proceed with its processing of the desired data included in the response 212.

Accordingly, in the example process flow 200, the correlation system 105 may provide requested information or data to the originating network (e.g., the EMR network 108) by accessing locally stored information or data 210 (e.g., information or data stored in the data storage entity 12) without requiring a respective transactional communication with the network that generated the requested data (e.g., the pharmacy network 102). Updates to the locally stored information or data may be initiated by the generating network (e.g., message 142 of FIG. 3B) as triggers occur. The updates initiated by the generating network, however, may be asynchronous and independent of data/information requests 208 generated by other networks (e.g., the EMR network 108). In this manner, the volume of inter-network messaging may be decreased.

With further regard to FIG. 3D, during the second example message exchange 205, the origination and the destination network roles may be reversed. In particular, the pharmacy network 102 may require data that is generated by the EMR network 108. Accordingly, the pharmacy network 102 may send a query 215 to the correlation system 105. The query 215 may include a request for patient-related data and/or network-related data that is generated by the EMR network 108 but is not available at the pharmacy network 102. Generally, queries 215 may include one or more requests for any patient-related data that is generated by or available on a network different from the originating network. For example, the query 215 may include a request for patient data that is included in a patient's electronic medical record. In some embodiments, a query 215 may additionally or alternatively include a request for network-related data that is specific to the destination network (e.g., data corresponding to EMR network 108). For example, the query 215 may include a request for an indication of whether or not a patient is eligible for a particular government drug program, such as an indication of information pertaining to patient visits to or encounters with qualified 340B program locations, and/or a request for an indication of time elapsed since the last patient visit to or encounter with a qualified 340B program location. The query 215 may include an indication of the target or destination network (e.g., the EMR network 108 and/or another network 8c-8n) from which the desired data may be obtained, but the inclusion of the indication of the destination network in the query 215 is optional.

The pharmacy network 102 may initiate the query when an electronic pharmacy program executing in the pharmacy network 102 requires information from the EMR network 108, such as from a particular patient's EMR. The electronic pharmacy program executing in the pharmacy network 102 may require information or data from the EMR network 108 to perform a pharmacy function such as filling a prescription; billing a prescription; counseling or dispensing advice with regard to proper or desired use of the prescription; counseling or dispensing advice with regard to possible adverse events with respect to the prescription; providing disease state management; monitoring drug therapy; and/or any other activity that is performed at a pharmacy location of the pharmacy network 102. Typically, but not necessarily, the pharmacy network 102 may initiate the query 215 based on a trigger corresponding to the pharmaceutical or pharmacy record of the particular patient. For example, the electronic pharmacy program may be a pharmacy billing program that requires an electronic check of whether or not the patient is eligible for a local, state or federal government program, such as 340B eligibility, and may initiate the query 215 while generating the bill. In another example, the electronic pharmacy program may operate in conjunction with a clinical aftercare program, a disease state management program, or a medication therapy management program in which the patient is participating, where at least a portion of the program(s) are tracked, managed, and/or executed electronically. Other examples of electronic pharmacy programs that execute at least part of a pharmacy function may be possible and may cause the pharmacy network 102 to generate or initiate a query 215 for information from another network.

The correlation system 105 may receive the query 215 from the originating network (e.g., the pharmacy network 102), and may retrieve 218 the requested information from one or more patient data files that are accessible to the correlation system 105 (e.g., from one or more patient data files stored in the data storage entity 12). The requested information may have been previously obtained from the EMR network 108 during a patient registration (e.g., message 132 of FIG. 3B) or a patient record update (e.g., message 138 of FIG. 3B). In an embodiment, the information obtained from the EMR network 108 may be stored in the one or more patient data files in a format utilized by the EMR network 108 (e.g., in a format compatible with an HL7 format). As the query 215 may be of a format different than that utilized by the EMR network 108, the correlation system 105 may map one or more fields of the query 215 with respective one or more fields of the one or more patient data files.

The correlation system 105 may generate a response 220 to the query 215, including formatting the requested information into a format that is known to the pharmacy network 102, e.g., in a format compatible with an NCPDP standard. The response 220 may be transmitted from the correlation system 105 to the originating network (e.g., to the pharmacy network 102), and the originating network may then proceed with its processing of the desired data included in the response 220.

Accordingly, in the example process flow 200, the correlation system 105 may provide requested information or data to the requesting network (e.g., the pharmacy network 102) by accessing locally stored information or data 218 (e.g., information or data stored in the data storage entity 12) without requiring a respective transactional communication with a network that generates the requested data (e.g., the EMR network 108). Updates to the locally stored information or data may be initiated by the generating network (e.g., message 138 of FIG. 3B) as triggers occur. The updates initiated by the generating network, however, may be asynchronous and independent of data/information requests 215 of other networks (e.g., the pharmacy network 102). In this manner, the volume of inter-network messaging may be decreased.

Any portions of the process flows 100, 130, 150 and 200 illustrated in FIGS. 3A-3D may be interspersed so that portions from different process flows occur during a same interval or time. That is, a particular process flow 100, 130, 150 and 200 need not be complete before a different process flow or another instance of the particular process flow begins. In one non-limiting example, the EMR network 108 may register 110 with the correlation system 105, and then may batch register 132 a plurality of patients. Subsequently, the pharmacy network 102 may register 115 with the correlation system 112, but prior to registering 135 any of its patients, the pharmacy network 102 may respond 162 to an EMR network query 155. In another non-limiting example, a pharmacy network 102 may register a batch of patients 135, and may update one of the patient's data 142 that was included in the batch registration 135 prior to the EMR network 108 registering 110 with the correlation system 105 at all. Of course, other examples of interleaving at least portions of one or more process flows 100, 130, 150 and 200 are possible.

Figure 4:
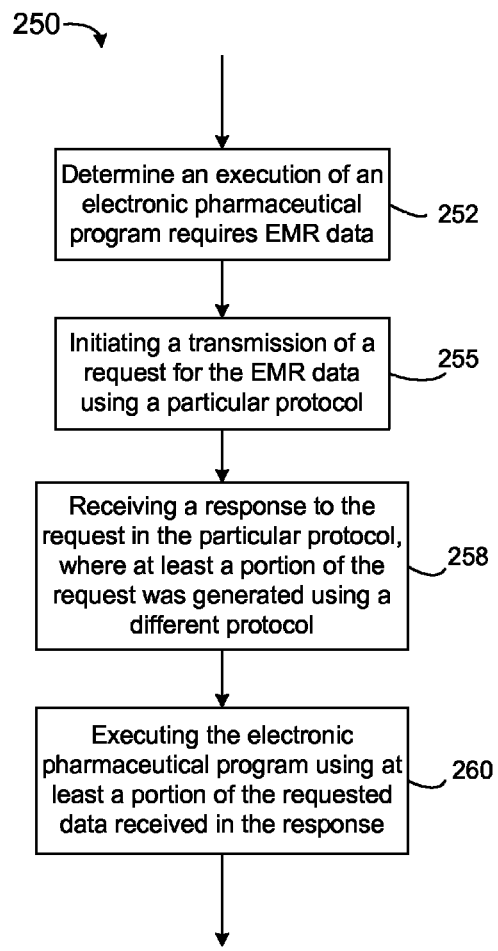
FIG. 4 is an example method for executing electronic pharmacy programs that require access to electronic medical records.

FIG. 4 is an example method 250 for executing electronic pharmacy programs that require access to electronic medical records. Embodiments of the method 250 may operate in conjunction with embodiments of the systems of FIGS. 1 and 2 and/or with embodiments of any number and/or portions of the process flows illustrated in FIGS. 3A-3D. In an embodiment, at least a portion of the method 250 is performed by a processor of a computing device executing computer-executable instructions, for example, the processor 55 of computing device 52 executing instructions 80 as shown in FIG. 2. For illustrative and not limiting purposes, the method 250 of FIG. 4 is discussed herein with simultaneous reference to the system 1 of FIG. 1, the computing device 52 of FIG. 2, and the process flows 100, 130, 150 and 200 of FIGS. 3A-3D, although the method 250 may operate in conjunction with other systems, computing devices, and/or process flows.

At a block 252, a determination may be made that an electronic pharmacy program requires data from an electronic medical record (EMR) during an execution of the electronic pharmacy program. In an embodiment, the electronic pharmacy program that requires data from an EMR corresponds to a patient with whom the EMR is associated. The electronic pharmacy program may include one or more functions that operate on a pharmaceutical or pharmacy record corresponding to the patient, in an embodiment, where the pharmaceutical or pharmacy record may be stored in a pharmacy data storage entity 10a of the pharmacy network 8a. In some embodiments, an electronic pharmacy program executing in the pharmacy network 102 may require information or data from an EMR that is accessible via the EMR network 108 to perform a pharmaceutical or pharmacy function or service, in a manner such as previously discussed.

With further regard to the block 252, the determination may be made at a computing device that is included in the pharmacy network 102, such as at a computing device 52, 70a, . . . , or 70n. In an embodiment, the computing device making the determination (block 252) may be the same computing device that is to execute the electronic pharmacy program, e.g., the computing device 52. In another embodiment, the computing device making the determination (block 252) may be a different computing device than the computing device that is to execute the electronic pharmacy program. For example, the computer-executable instructions for determining that an electronic pharmacy program may be included in the instructions 80 in the memory 58 of computing device 52, while the computer-executable instructions for executing the electronic pharmacy program 82 may be stored in a memory of another computing device 70a-70n within the pharmacy network 8a.

Typically, the EMR from which the desired data may be obtained may be stored on a network other than the pharmacy network 102 (e.g., in EMR data storage 10b in the EMR network 108), and the desired data may be obtained or accessed using a protocol or format that is different than the protocol or protocols used by the pharmacy network 102. In an embodiment, the EMR may be accessible by using a protocol that is at least partially based on an HL7 standard, while the protocol used by the pharmacy network may be at least partially based on an NCPDP standard.

At a block 255, a transmission of a request for the desired EMR data may be initiated by the pharmacy network 102 (e.g., by a computing device 52, 70a, . . . , or 70n included in the pharmacy network 102). In an embodiment, the computing device that initiates the transmission of the request (block 255) may be the same computing device that is to execute the electronic pharmacy program, and may be the same computing device that made the determination of the EMR data requirement (block 252). In another embodiment, the computing device that that initiates the transmission of the request (block 255) may be a different computing device than the computing device that is to execute the electronic pharmacy program, or may be a different computing device than the computing device that made the determination of the EMR data requirement (block 252).

Initiating the transmission of the request for desired EMR data (block 255) may include initiating a transmission of the request to a destination network via which the EMR may be accessed. Typically, but not necessarily, the destination network may be external to the pharmacy network 102, e.g., the EMR network 108, and may be accessed via an external network interface 78. In an embodiment, the destination network is selected or identified from a plurality of destination networks 8a-8n, where each of the plurality of destination networks 8a-8n corresponds to a different health care organization. For example, a first destination network may correspond to a hospital, a second destination network may correspond to an electronic medical record data warehouse or clearing house, a third destination network may correspond to a physical and occupational therapy practice, etc. In an embodiment, a computing device included in the pharmacy network 102 (e.g., the computing device 52, 70a, . . . , or 70n) may determine the identity of the destination network and may include the determined identity of the destination network in the request, but the inclusion of the determined destination network identity in the request is not required. In an embodiment, an identification of the patient with whom the EMR is associated may be alternatively or additionally included in the request.

At a block 258, a response to the request may be received. The response to the request may be received at the computing device that initiated the transmission of the request (block 255) or at another computing device included in the pharmacy network 102. The received response may be in the protocol or format utilized by the pharmacy network 102, however, at least a portion of the contents of the response (e.g., at least a portion of the requested EMR data) may have been accessed from the EMR using the protocol or format utilized by the destination network. Furthermore, at least a portion of the response may have been originated or generated by the destination network using the protocol or format utilized by the destination network. In embodiment, the response may be received via the external network interface 78.

In some embodiments, at least a portion of the received response may be stored. For example, contents of the response corresponding to the desired request may be temporarily or permanently stored, along with desired administrative information corresponding to the requested data, e.g., a timestamp, message header information, and the like. The data and information corresponding to the response may be stored in conjunction with the pharmaceutical or pharmacy record of the patient, in an embodiment.

At a block 260, at least the part of the electronic pharmacy program determined at the block 252 to require EMR data may be executed using at least a portion of the contents from the request received at the block 258. The at least the part of the electronic pharmacy program may be executed by the same computing device at which the response was received (block 258), or the at least the part of the electronic pharmacy program may be executed by another computing device that did not receive the response (block 258) but is included in the pharmacy network 102.

Although the foregoing text sets forth a detailed description of numerous different embodiments, it should be understood that the scope of the patent is defined by the words of the claims set forth at the end of this patent. The detailed description is to be construed as exemplary only and does not describe every possible embodiment because describing every possible embodiment would be impractical, if not impossible. Numerous alternative embodiments could be implemented, using either current technology or technology developed after the filing date of this patent, which would still fall within the scope of the claims.

Thus, many modifications and variations may be made in the techniques and structures described and illustrated herein without departing from the spirit and scope of the present claims. Accordingly, it should be understood that the methods and apparatus described herein are illustrative only and are not limiting upon the scope of the claims.

What is claimed is:

1. A method of transferring electronic pharmacy information and electronic medical record information, the method comprising:

determining, at a first computing device, that an execution of at least a part of an electronic pharmacy program requires first data that is included in an electronic medical record (EMR) corresponding to a patient, wherein the EMR is stored in a storage device, and the first data included in the EMR is accessed using a first protocol;

initiating, by the first computing device and using a second protocol different from the first protocol, a transmission of a request for the first data included in the EMR to a first computing system, the first computing system storing the first data included in the EMR;

receiving, at the first computing device, a response to the transmitted request, the received response being compatible with the second protocol and including the requested first data, wherein the requested first data was accessed from the EMR using the first protocol;

executing, by the first computing device or by a second computing device in communicative connection with the first computing device, the at least the part of the electronic pharmacy program using the requested first data included in the received response;

receiving, at the first computing device, a request for second data stored at a pharmacy network, the pharmacy network storing pharmacy records corresponding to patients, the first computing device and the second computing device included in the pharmacy network, and the pharmacy network different from the first computing system, wherein:

the received request for the second data is based on a query generated by a second computing system different from the pharmacy network, and the second computing system includes the storage device storing one or more EMRs including the EMR corresponding to the patient; and causing, by the first computing device, the requested second data to be included in a generated response to the query, the generated response to be transmitted to the second computing system.

2. The method of claim 1, wherein initiating the transmission of the request for the first data comprises initiating the transmission of a request that includes at least one of an identification corresponding to the patient or an identification of the second computing system.

3. The method of claim 1, further comprising receiving, at the first computing device, a communication from the first computing system, wherein the communication is received at the first computing device using the second protocol, and wherein at least a portion of contents of the communication was originated using the first protocol.

4. The method of claim 1, wherein executing the at least the part of the electronic pharmacy program comprises executing at least a part of: an electronic check for eligibility of the patient, a clinical aftercare program corresponding to the patient, a medication therapy management program corresponding to the patient, a disease state management program corresponding to the patient, or a function that operates on a pharmacy record corresponding to the patient and stored at the pharmacy network.

5. The method of claim 1, wherein the first protocol is based on a Health Level Seven International (HL7) protocol.

6. The method of claim 1, wherein the second protocol is based on a National Council for Prescription Drug Programs (NCPDP) standard.

7. The method of claim 1, wherein the requested second data is stored at the pharmacy network in a particular pharmacy record corresponding to a respective patient.

8. The method of claim 1, wherein the query is generated by the second computing system using the first protocol, and wherein the generated response to the query is compatible with the second protocol.

9. A system for transferring electronic pharmacy information and electronic medical record information, the system comprising:

a first data storage device included in a pharmacy network and storing a pharmacy record corresponding to a patient;

a network interface; and one or more computing devices included in the pharmacy network and coupled to the data storage device, the one or more computing devices configured to initiate an execution of an electronic pharmacy program, the execution of the electronic pharmacy program being based on first data included in the pharmacy record corresponding to the patient;

the one or more computing devices configured to determine that an execution of at least a part of the electronic pharmacy program requires second data that is included in an electronic medical record (EMR) corresponding to the patient and that is stored on a second data storage device excluded from the pharmacy network;

the one or more computing devices configured to initiate, using a first protocol, a transmission of a request for the second data included in the EMR corresponding to the patient from the system for transferring electronic pharmacy information and electronic medical record information via the network interface;

the one or more computing devices configured to receive, using the first protocol via the network interface at the system for transferring electronic pharmacy information and electronic medical record information, the requested second data, wherein the requested second data was accessed from the EMR corresponding to the patient using a second protocol;

the one or more computing devices configured to execute the at least the part of the electronic pharmacy program based on the requested second data;

the one or more computing devices configured to receive a request for third data stored at the first data storage device, wherein the received request for the third data is based on a query generated by a second computing system, the second computing system storing one or more EMRs including the EMR corresponding to the patient; and the one or more computing devices configured to cause the requested third data to be included in a generated response to the query, the generated response to be transmitted to the second computing system.

10. The system of claim 9, wherein the transmitted request for the second data that is included in the EMR includes an identification of the second computing system storing the EMR corresponding to the patient.

11. The system of claim 9, wherein the transmitted request for the second data that is included in the EMR includes an identification of the patient.

12. The system of claim 9, wherein the first protocol is compatible with a National Council for Prescription Drug Programs (NCPDP) standard, and the second protocol is compatible with a Health Level Seven International (HL7) format.

13. The system of claim 9, the one or more computing devices are further configured to:

receive, from a correlation system and using the second protocol, a communication corresponding to the patient, wherein at least some of contents of the communication were originated by the second computing system using the first protocol; and store at least a portion of data included in the communication in conjunction with the pharmacy record corresponding to the patient.

14. The system of claim 9, wherein the third data is stored in the pharmacy record corresponding to the patient or is stored in another pharmacy record corresponding to another patient.

15. The system of claim 9, wherein:
the query generated by the second computing system is compatible with the second protocol; and
the generated response to the query generated by the second computing system is compatible with the first protocol.

* * * * *